(12) United States Patent
Curti

(10) Patent No.: US 9,604,024 B2
(45) Date of Patent: Mar. 28, 2017

(54) DIVIDED CANNULA WITH EACH NARE COMMUNICATING WITH EACH FLOW PATH

(75) Inventor: James N. Curti, Bakersfield, CA (US)

(73) Assignee: Salter Labs, Arvin, CA (US)

( * ) Notice: Subject to any disclaimer, the term of this patent is extended or adjusted under 35 U.S.C. 154(b) by 895 days.

(21) Appl. No.: 13/823,909

(22) PCT Filed: Sep. 16, 2011

(86) PCT No.: PCT/US2011/051952
§ 371 (c)(1),
(2), (4) Date: Apr. 26, 2013

(87) PCT Pub. No.: WO2012/037469
PCT Pub. Date: Mar. 22, 2012

(65) Prior Publication Data
US 2013/0211275 A1    Aug. 15, 2013

Related U.S. Application Data

(60) Provisional application No. 61/383,970, filed on Sep. 17, 2010.

(51) Int. Cl.
*A61M 16/00*    (2006.01)
*A61B 5/097*    (2006.01)
*A61M 16/06*    (2006.01)

(52) U.S. Cl.
CPC ......... *A61M 16/0666* (2013.01); *A61B 5/097* (2013.01); *A61M 16/0057* (2013.01); *A61M 16/0677* (2014.02)

(58) Field of Classification Search
CPC .............. A61B 5/097; A61M 16/0666; A61M 16/0057; A61M 16/0677; A61M 15/08; A61M 2016/0672
(Continued)

(56) References Cited

U.S. PATENT DOCUMENTS 4,457,303 A    7/1984 Durkan
4,462,398 A    7/1984 Durkan et al.
(Continued)

OTHER PUBLICATIONS

International Search Report dated Apr. 26, 2012.
Written Opinion dated Apr. 26, 2012.

*Primary Examiner* — Kathryn E Ditmer
(74) *Attorney, Agent, or Firm* — Michael J. Bujold; Davis & Bujold, PLLC

(57) ABSTRACT

A divided cannula comprising a cannula body which is divided by a partitioning wall into first and second flow chambers. The first flow chamber has first and second spaced apart nare passages while the second flow chamber has first and second spaced apart nare passages. The cannula body supports spaced apart first and second nares and each of the first and the second nares defines a common nare passage. The first nare passage of the first internal flow chamber and the first nare passage of the second internal flow chamber both communicate with the common nare passage of the first nare and the second nare passage of the first internal flow chamber and the second nare passage of the second internal flow chamber both communicate with the common nare passage of the second nare. A pressure sensing line and a gas supply line interconnected to the divided cannula with a gas supply system.

11 Claims, 4 Drawing Sheets

(58) Field of Classification Search
USPC .......................... 128/203.18, 207.18, 206.11
See application file for complete search history.

(56) References Cited

U.S. PATENT DOCUMENTS

| | | | |
|---|---|---|---|
| 4,584,996 A | | 4/1986 | Blum |
| 4,612,928 A | | 9/1986 | Tiep et al. |
| 4,686,974 A | | 8/1987 | Sato et al. |
| 4,686,975 A | | 8/1987 | Naimon et al. |
| 4,706,664 A | | 11/1987 | Snook et al. |
| 4,989,599 A | | 2/1991 | Carter |
| 5,099,836 A | | 3/1992 | Rowland et al. |
| 5,375,593 A | * | 12/1994 | Press .................. 128/207.18 |
| 6,089,229 A | * | 7/2000 | Bathe .................. A61M 16/12 |
| | | | 128/203.12 |
| 6,655,385 B1 | | 12/2003 | Curti et al. |
| 6,799,575 B1 | | 10/2004 | Carter |
| 2005/0121033 A1 | * | 6/2005 | Starr ................ A61M 16/1065 |
| | | | 128/204.18 |

* cited by examiner ously monitor a parameter of the patient's breathing cycle, such as pressure, gas concentration, etc. ---

DIVIDED CANNULA WITH EACH NARE COMMUNICATING WITH EACH FLOW PATH

The present application is a national phase application of PCT Application No. PCT/US2011/051952, filed on Sep. 16, 2011, and claims priority to U.S. provisional application 61/383,970, filed Sep. 17, 2010.

FIELD OF THE INVENTION

The present invention relates to an improved divided cannula and, in particular, for a divided cannula having two separate passages for concurrent monitoring of a parameter of a patient's breathing cycle and the delivery of therapeutic gas.

BACKGROUND OF THE INVENTION

Medical situations such as the treatment of respiratory problems as well as a wide range of other medical conditions frequently require the delivery of a therapeutic gas(es), such as supplemental oxygen, to a patient or the monitoring of a patient's breathing or exhaled gases, or any combination thereof. The delivery of gases to a patient and the monitoring of a patient's breathing are commonly performed through cannulas, which are typically assemblies of tubes positioned adjacent a patient's nasal passages to deliver gas(es) to or sense breathing via the nostrils.

A cannula for delivering a therapeutic gas to a patient or capturing samples of exhaled breath from a patient, or both, is positioned horizontally between and adjacent to the patient's nose and typically includes an elongated body having an internal gas passage within the cannula body. A cannula typically includes at least one and often two hollow nares that extend upward from the cannula body and the internal gas passage therein and into corresponding ones of the patient's nasal passages to form gas flow paths between the patient's respiratory system, the gas passage within the cannula body and one or more gas delivery and/or sampling lines connected to the body of the cannula and the gas passage therein. In addition, the internal gas passage in the hollow body of a cannula may be divided into first and second halves by an internal septum or partition wall extending across the internal gas passage, thereby dividing the internal gas passage into two, separate gas flow paths and allowing, for example, samples of exhaled breath to be captured on one side of the cannula while permitting a treatment gas to be provided to the patient via the other side of the cannula.

There are essentially two primary methods or systems for delivering a therapeutic gas, such as oxygen, to a patient one of which is referred to as a continuous or constant flow system and the other of which is commonly referred to as an on-demand system. A continuous flow system simply provides a continuous flow of gas to the patient through either or both nares of a cannula. A continuous flow system is thereby relatively simple in operation, needing only a single nare to deliver the gas to the patient and requiring only that the flow of gas be monitored so as to ensure that a flow of gas, at the desired flow volume, continues to flow to the cannula, while the use of multiple nares to deliver the gas reduces the possibility that the flow of gas will be completely interrupted by blockage of any one of the nares. The relative simplicity and possibly lower associated equipment costs of a continuous flow system tend to be offset, however, by the significant costs of providing a continuous flow of gas, including during those portions of the patient's breathing cycle when the patient is not inhaling. Much of the gas is thereby exhausted directly into the surrounding environment and thus wasted.

An on-demand system delivers gas to the patient only during the inhalation portion of the patient's breathing cycle by sensing pressure changes via the cannula, during the patient's breathing cycle, and initiating a timed release or bolus of gas to the patient such that the gas is delivered to the patient at the start of and during the next inhalation breath of the patient's breathing cycle. An on-demand system thereby requires at least one pressure sensing connection to the cannula, e.g., to a nare, in order to monitor and sense pressure changes during the patient's breathing cycle, and one or more gas delivery connections to in the cannula, again to a nare for delivering the gas to the patient.

Examples of "on demand" systems include U.S. Pat. No. 4,462,398 and U.S. Pat. No. 4,519,387 to Durkan et al. wherein a control circuit, responsive to a sensor, operates a valve to supply pulses of respirating gas through a single hose cannula to a respiratory system of a patient when a negative pressure, indicative of the initial stage of inhalation or inspiration, is sensed by the sensor. The pulse of gas delivered to the respiratory system can have a preselected pulse profile. This method provides for supplying a fixed volume of supplemental respiratory gas per unit of time. The volumetric flow rate of the supplemental respiratory gas is preset and the time duration of each application of the supplemental respiratory gas is also preselected, thereby providing a fixed volume of respiratory gas after the beginning of inhalation. Also, this method provides for a minimal delay interval between successive applications of respiratory gas and such delay interval is also predetermined since the time interval for respiratory gas flow is preset for a time less than the time of the inspiration.

Another prior art supplemental oxygen delivery system designed to conserve respiratory gas by delivering oxygen "on demand" only during inhalation is described in U.S. Pat. No. 4,612,928 to Tiep et al. which discloses both a method and apparatus for supplying a gas to a body. The apparatus and method are employed to minimize the amount of oxygen needed to maintain a specific oxygen concentration level in the blood of an individual. The apparatus includes a transducer and other circuit components to obtain a first series of pulses or signals corresponding to the individual's breath rate. A divider or counter processes the signals or pulses of the first series to create a second series of pulses or signals corresponding to periodic pulses or signals of the first series. The pulses or signals of the second series are used to periodically open a valve to deliver oxygen to the individual at about the start of the inhalation interval of the individual's periodic breathing cycles.

Further examples of the prior art, such as U.S. Pat. Nos. 4,457,303 and 4,484,578, recognize that oxygen delivered at the end of the inhalation interval of the breathing cycle is wasteful. These two patents describe respirator apparatuses and methods therefor. In brief, a fluidically-operated respirator comprises an apneic event circuit and a demand gas circuit. The apneic event circuit comprises a variable capacitance device and an exhaust means which rapidly discharges fluid from the circuit when inhalation occurs. The demand gas circuit of the respirator supplies the respirating gas to a patient at the beginning of inhalation and for a time period which is a fraction of the duration of the inhalation. Thus, these patents also follow the reasoning that insufflation at the beginning of inhalation will effectively supply the respirating gas to the patient.

In yet another prior art system, described in U.S. Pat. No. 4,686,974 to Sato et al., a supplemental oxygen delivery system begins to deliver a steady flow of oxygen during a later stage of the exhalation interval and through an advanced stage of the inhalation interval of the breathing cycle and superimposes upon this steady flow of oxygen a peak pulse flow of oxygen at the beginning of inhalation. This device includes a gas source, a valve, an insufflating device, a sensor, and an operational controller. The valve is connected to the gas source so as to regulate flow rate and duration of the gas flow from the gas source. The insufflating device is connected to the valve so as to insufflate the gas therefrom toward a respiratory system of a living body. The sensor is exposed to respiration of the living body and produces electric signals which must distinctively indicate an inhalation interval and an exhalation interval of the breathing cycle. The operational controller receives the electric signals from the sensor and produces control signals to the valve so that gas insufflation starts before the beginning of the inhalation interval and ends before termination of the inhalation interval while providing a short pulse-like peak flow of a large amount of the gas in an early stage of the inspiratory interval. Specifically, steady insufflation of the gas starts before the beginning of each inhalation and the pulse-like peak flow insufflation of the gas is superimposed on the steady insufflation for a short period of time after the beginning of the inhalation. An arbitrary time interval, based upon an average exhalation period and an average inhalation period, is chosen to trigger and end insufflation during the breathing cycle.

Although the prior art devices discussed hereinabove indeed conserve delivery of a treatment gas, such as oxygen, they generally fail to address the problem related to the changing respiratory needs of the patient that vary with different patient activity levels. When a patient requiring supplemental oxygen is at rest, relatively small quantities of oxygen, are required in order to maintain appropriate levels of oxygen concentration in the blood and thereby prevent what is commonly termed "desaturation". With an increase in the physical activity of a patient, generally larger quantities of oxygen are required in order to maintain appropriate levels of oxygen concentration in the blood of the patient compared to when the patient is at rest.

Such systems are generally referred to as "on the go" systems and an example of such is U.S. Pat. No. 4,706,664 wherein Snook et al. discloses a pulse-flow supplemental oxygen apparatus which yields savings in oxygen while affording the patient the physiological equivalent of a prescribed continuous stream of oxygen. The apparatus includes a demand oxygen valve operated in a pulse mode by electronic control circuitry. Through an appropriate sensor, the electronic control circuitry monitors the patient's breathing efforts and gives a variable timed pulse of oxygen to increase the volume delivered to the patient during the very initial stage of each inhalation interval of the breathing cycle or breath. Pulse volume variability is based upon a measured parameter characterizing a plurality of the patient's preceding breathing cycles. The elapsed time interval of the patient's three preceding breathing cycles is measured to effectively measure the rate of the breathing cycles. These breath-characterizing parameters, together with data characterizing the prescribed continuous oxygen flow to be matched, enable the apparatus to give the desired dose variability.

In yet another example, U.S. Pat. No. 4,584,996 to Blum reveals a method and apparatus for intermittent administration of supplemental oxygen to patients with chronic lung dysfunction. The apparatus is programmable for administering the specific oxygen requirements of the patient and is responsive to changes in these oxygen requirements with increased patient activity. The patient's arterial blood oxygen level is measured while supplying oxygen to the patient during inspiration to determine the number of breathing cycles required to reach a first higher arterial blood oxygen level and is again measured without supplemental oxygen to determine the number of breathing cycles required to diminish the arterial blood oxygen level to a second, lower level. These two cycle numbers are utilized in an algorithm which is applied as a program to the apparatus having a breathing cycle sensor, a counter and control valve. The control valve provides a regulated flow of supplemental oxygen to a nasal cannula for a predetermined number of "ON" breathing cycles and to shut off the flow for a preset number of "OFF" breathing cycles sequentially and repetitively, thereby conserving oxygen while medically monitoring the patient's blood oxygen levels. The oxygen conservation features of this apparatus are further enhanced by turning off the oxygen flow during the exhalation interval of each breathing cycle throughout the "ON" breathing cycles. As the respiratory rate of the patient increases with patient activity, the duration of the "ON" and "OFF" periods changes accordingly.

In U.S. Pat. No. 4,686,975, Naimon et al. teaches a supplemental respiratory device that uses electronic components to intermittently regulate the flow of a respirable gas to a user on a demand basis. By monitoring small changes in the relative airway pressure, this respiratory device supplies gas only when an inhalation is detected. This respiratory device can also vary the duration of the gas delivery time to compensate for changes in the user's breath rate, thereby attempting to adjust for changes in the patient's respiratory needs based upon activity.

U.S. Pat. No. 5,099,836, issued to Rowland et al. on Mar. 31, 1992, relates to a cannula body which supports a pair of spaced apart nares. Each one of the nares has a dividing wall which separates each one of the nares of the cannula into two completely separate flow outlets. A first half of each nare, due to the dividing wall, communicates with the internal flow chamber of the main body of the cannula while a second half of each nare does not communicate with the internal flow chamber but instead communicates, via a side port provide in the side wall of each nare, with a sensing device. The internal flow chamber of the main body of the cannula is connected to a gas supply source, via a first set of tubes, while the sensing device is coupled to the nares of the cannula, by a second set of separate tubes. The dividing wall, within the flares, extends all the way to the inlet/outlet of each nare so that neither one of the nares has a common flow region within the nare and adjacent the inlet/outlet of each nare. As a result of such design, the cannula according to this patent is generally not a divided cannula, that has two internal flow chambers, and is generally cumbersome to utilize due to the additional set of tubes as well as its overall complexity.

A number of other "on demand" and "on the go" systems and cannulas are currently available in the market and Salter Labs, the assignee, of the above identified application, is one supplier of such products.

There are many other examples of "on demand" and "on the go" systems as many manufacturers are marketing oxygen conserver devices which are adapted to retrofit onto typical supplemental oxygen delivery systems that employ any type of oxygen source, such as portable oxygen tanks, oxygen concentrators or wall outlet supplies often utilized in hospitals. These oxygen conserver devices are adapted to be interposed between the oxygen source and a conventional nasal cannula apparatus. Medisonic U.S.A., Inc. of Clarence, N.Y., manufactures an oxygen conserver device entitled MedisO$_2$ nic Conserver. It conserves oxygen by interrupting the flow of oxygen from the source to the patient during the exhalation interval of the patient's breathing cycle. Chad Therapeutics, Inc. of Chatsworth, Calif., manufacturers an oxygen conserver device bearing a registered trademark, Oxymatic® Electronic Oxygen Conserver. Chad's oxygen conserver eliminates oxygen waste during both the exhalation interval and the later portion of the inhalation interval of the breathing cycle. TriTec, Inc. of Columbia, Md., manufactures a demand oxygen cannula for portable oxygen systems that also responds to the negative pressure of inhalation. Smith-Perry Corporation of Surrey, British Columbia, Canada, manufactures The VIC (Voyager Intermittent Controller) Breathsaver that senses every breath of the patient and delivers a measured dose of oxygen only when the patient inhales. Pulsair, Inc. of Fort Pierce, Fla., manufactures an oxygen management system that delivers oxygen to the patient "on demand" at the initiation of inhalation. The Henry G. Dietz Co., Inc. of Long Island City, N.Y., manufactures an oxygen conserver device entitled Hala'tus 1 which conserves oxygen by sensing when inhalation takes places and delivers the oxygen only during inhalation.

While an on-demand or on the go system thereby offers significant reduced costs in terms of gas delivered, in return for increased system complexity and costs, a recurring problem in on-demand systems is the risk that one or more nares may become blocked due, for example, to nasal or respiratory discharges. That is, an on-demand or on the go system employs the cannula nares as the pressure sensing and gas delivery passages.

Conventional cannulas of the prior art, when used for on-demand and on the go systems, however, include only two nares, one of which is used to sense changes in pressure during the patient's breathing cycle to thereby detect the exhalation portion of the breathing cycle and the other of which is used to deliver gas to the patient. If the pressure sensing nare become blocked or occluded for some reason, therefore, the system will cease delivery of gas to the patient because the exhalation portion of the respiratory cycle cannot be detected, so that the delivery of gas cannot be triggered. If, on the other hand, the gas delivery nare becomes blocked, the gas cannot be delivered to the patient even if the gas delivery cycle is suitably triggered.

Lastly, it must be noted that the above described problems with cannulas of the prior art are not confined solely to on-demand gas delivery systems for oxygen and other gases that are triggered by sensing pressure changes during a patient's respiratory cycle. Such problems may appear, for example, in any system requiring the concurrent use of two or more separate passages of the cannula, such as the sensing of a parameter of a patient's respiratory cycle or other medical condition and the concurrent delivery of gas to the patient. Such systems may include, for example, a system for the delivery of oxygen dependent upon the patient's sensed exhaled $CO_2$ levels or a system that monitors the breathing of a patient while concurrently delivering therapeutic gas to a patient independently of the patient's breathing cycle or medical condition, such as a system for monitoring sleep apnea. Others of such systems may include, for example, systems delivering multiple gases and requiring multiple gas delivery paths or systems monitoring multiple aspects of a patient's breathing cycle or medical condition and requiring multiple monitoring paths, or both.

The present invention provides a solution to these as well as other related problems of the prior art.

SUMMARY OF THE INVENTION

The present invention is directed to a divided cannula for the concurrent monitoring of a parameter of a patient's breathing cycle and the delivery of a therapeutic gas to the patient and to a system for providing gas to a patient via a divided cannula.

It is an object of the invention to provide a divided cannula in which both the first and second internal flow chambers communicate with each one of the nares of the divided cannula so that a blockage in either of the nares will not hinder flow through either one of the first and second internal flow chambers.

The present invention also relates to a divided cannula comprising a cannula body being divided by a partitioning wall into first and second flow chambers; the cannula body supporting spaced apart first and second nares and each of the first and the second nares defining a common nare passage; and the common nare passage of the first nare communicating with both of the first and the second internal flow chambers, and the common nare passage of the second nare communicating with both of the first and the second internal flow chambers.

The present invention also relates to a system for providing gas to a patient, comprising a divided cannula comprising a cannula body being divided by a partitioning wall into first and second flow chambers and the first flow chamber has a first connection section adjacent one end of the divided cannula and the second flow chamber has a second connection section adjacent another end of the divided cannula, the first flow chamber having first and second spaced apart nare passages, the second flow chamber having first and second spaced apart nare passages, the cannula body supporting spaced apart first and second nares and each of the first and the second nares defining a common nare passage, and the first nare passage of the first internal flow chamber and the first nare passage of the second internal flow chamber both communicate with the common nare passage of the first nare and the second nare passage of the first internal flow chamber and the second nare passage of the second internal flow chamber both communicate with the common nare passage of the second nare, and a pressure sensing line is connected with the first connection section and a gas supply lihe is connected with the second connection section and opposite ends of both the pressure sensing line and the gas supply line are connected with a gas supply system.

BRIEF DESCRIPTION OF THE DRAWINGS

The invention will now be described, by way of example, with reference to the accompanying drawings in which.

DETAILED DESCRIPTION OF THE INVENTION

Figure 1:
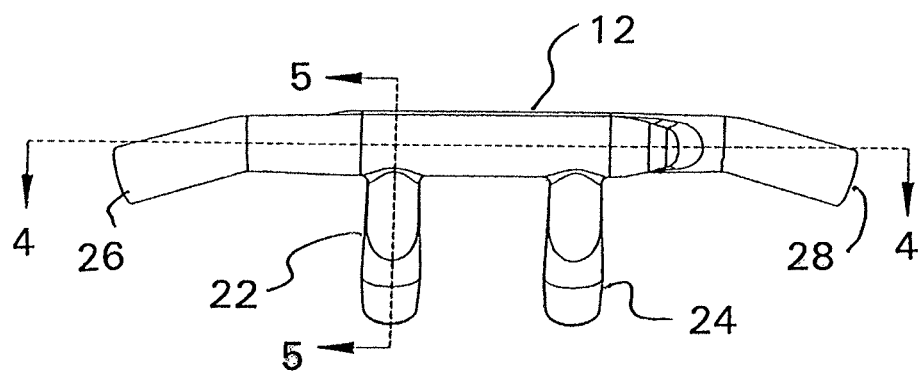
FIG. 1 is a diagrammatic front elevational view of a divided cannula according to the present invention.
Figure 2:
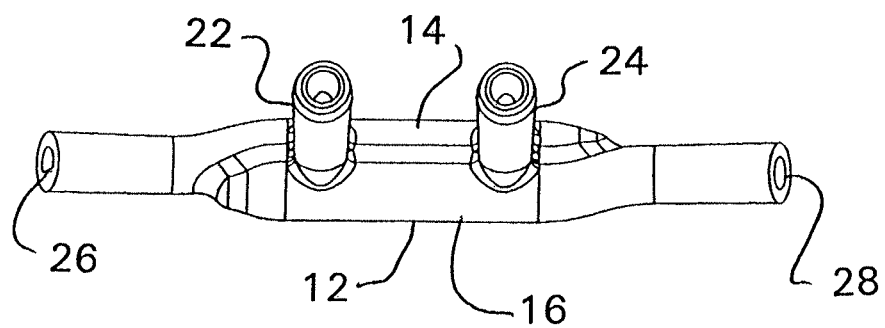
FIG. 2 is a diagrammatic top plan view of the divided cannula of FIG. 1.
Figure 3:
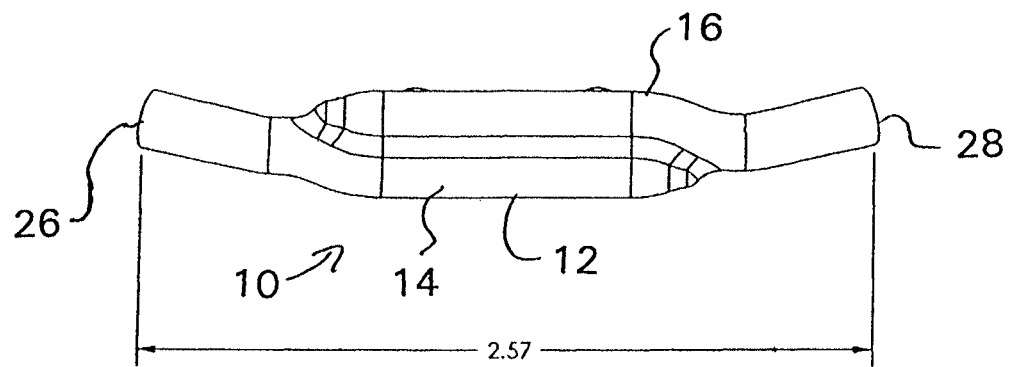
FIG. 3 is a diagrammatic bottom plan view of the divided cannula of FIG. 1.
Figure 6:
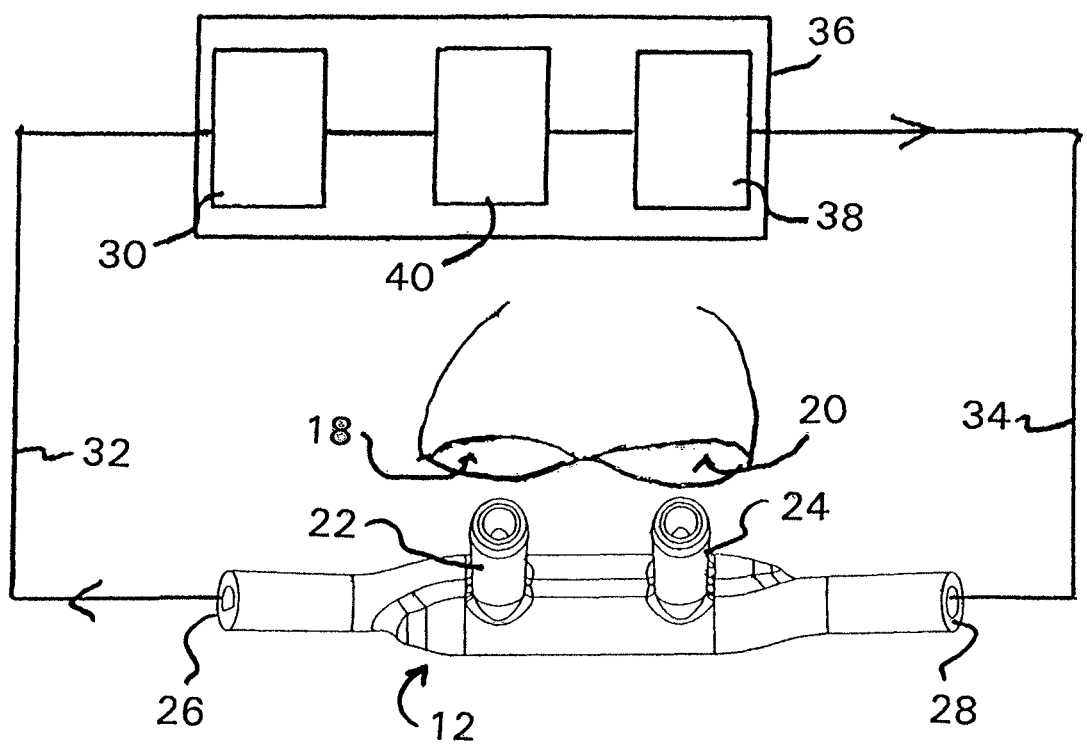
FIG. 6 is a diagrammatic representation showing use of the divided cannula according to the present invention.

Referring to FIGS. 1, 2 and 3, front, top and bottom views of a divided cannula 10, according to the present invention, are respectively diagrammatically shown. As shown illustrated therein, the divided cannula 10 includes a cannula main body 12 having overlapping, horizontally disposed first and second divided body sections 14 and 16, both being divided and separated from one another by a common axially extending partitioning or dividing wall 17 in which the first divided body section 14 is located generally on a first side of the cannula main body 12 as well as a patient's nasal passages 18 and 20 while the second divided body section 16 is located on a second opposite side of the cannula main body 12 as well as the patient's nasal passages 18 and 20. As shown best in FIG. 2, each of first and the second divided body sections 14 and 16 extends and terminates at a point generally a short distance past the respective nare 22 or 24, and thus the patient's opposing nasal passage 20, 18 so that, during use of the divided cannula 10, each of the patient's nasal passages 20, 18 will be located so as to facilitate communication with both of the first and the second divided body sections 14 and 16, as will be discussed below in further detail. The opposite end of each of first and the second divided body sections 14 and 16 has a corresponding connection section 26, 28, e.g., an open end located at each opposed end of the divided cannula 10 for connection to a desired tubing or line, as generally illustrated in FIG. 6 and described below in further detail, that allows connection to either a breathing sensor system 30, via a pressure sensing line 32, or to a gas source 38 and a gas controller 40, via a gas supply line 34 of a gas supply system 36.

Figure 4:
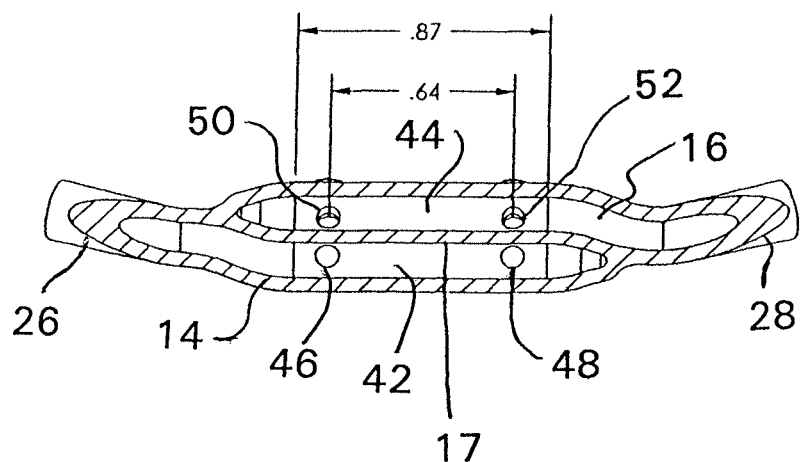
FIG. 4 is a longitudinal cross sectional bottom view of the divided cannula along the cross section line 4-4 of FIG. 1.
Figure 5:
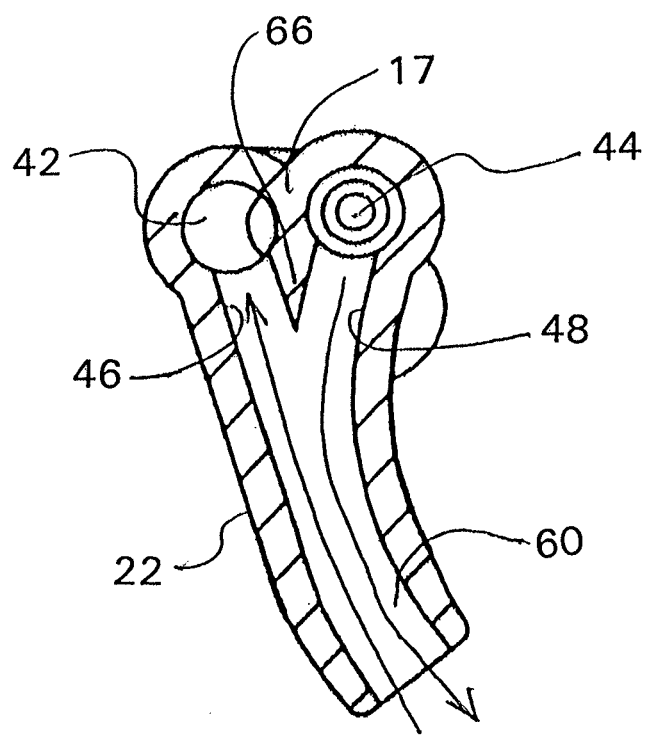
FIG. 5 is a transverse cross sectional view of the divided cannula along the cross section line 5-5 of FIG. 1.

Referring to FIGS. 4 and 5, further details concerning the internal structure of the divided cannula 10 of the present invention will now be discussed. As shown in FIG. 4, the first divided body section 14 defines a first interior flow chamber 42 while the second divided body section 16 defines a second interior flow chamber 44, and each of the first and the second flow chambers 42, 44, extends to and communicates with a respective one the first and the second connection sections 26 and 28 to form respective flow paths between the flow chamber 42, 44 and the corresponding connection sections 26 and 28. The first divided body section 14 further includes a first and second spaced apart nare passages 46 and 48 which both communicate with the first interior flow chamber 42 while the second divided body section 16 also includes first and second spaced apart nare passages 50 and 52 which both communicate with the second interior flow chamber 44. As shown in FIG. 5, the first nare passage 46 of the first flow chamber 42 and the first flare passage 50 of the second flow chamber 44 both communicate with a single common nare passage 60 of the first nare 22, and such connection is described below in further detail, while the second nare passage 48 of the first flow chamber 42 and the second nare passage 52 of the second flow chamber 44 both communicate with a common interior passage 60 of the second nare 24, also described below in further detail. As a result of such arrangement, the first and the second flow chambers 42 and 44, of the first and the second divided body sections 14 and 16 and thereby the sensing line 32 and gas supply line 34 of the gas supply system 36, are thus each connected with both the first nare 22 and with the second nare 24, via the divided cannula 10 according to the present invention.

Referring next to FIG. 5, this cross sectional view shows further details of the interior structure of the first nare 22 and the connection between the first flow chamber 42 of the first divided body section 14 with the first nare 22 as well as the connection between the second flow chamber 44 of the second divided body section 16 with the first nare 22. It is to be understood that the connection between the second flow chamber 44 of the second divided body section 16 with the second nare 24 is in a similar manner. As shown in FIG. 5, the interior of the first nare 22 generally has a Y-shaped interior passage comprising the common nare passage 60 which bifurcates and communicates with both the first nare passage 46, of the first flow chamber 42, and the first nare passage 50, of the second flow chamber 44. Similarly, but not shown in any of the Figures, the interior of the second nare 24 generally has a Y-shaped interior passage having the common nare passage 60 which bifurcates and communicates with the second nare passage 48, of the first flow chamber 42, and with the second nare passage 52, of the second flow chamber 44.

As also shown in FIG. 5, the first nare passage 46 of the first flow chamber 42 and the first nare passage 50 of the second flow chamber 44 are separated from one another by a tapering flow diverter wall 66, which is generally an extension of the common axially extending partitioning or dividing wall 17 and feathers or tapers toward the remote free end of the respective nare 22 or 24. The flow diverter wall 66 assists with dividing and forming two separate flow paths, one through the first nare passage 46, of the first flow chamber 42, and into the first flow chamber 42 and other through the first nare passage 50, of the second flow chamber 44, and into the second flow chamber 44, with one of these two flow paths functioning so as to permit a flow of a gas into the divided cannula 10 and the other of the two flow paths functioning so as to permit flow out of the divided cannula 10.

As shown in FIG. 6, the nares 22 and 24 of the divided cannula 10 extend generally upward, during use, from the cannula main body 12 and are generally located so that the remote free end of each of the nares 22 and 24 is partially received by and extends into a respective one of the patient's nasal passages 18 and 20. The opposed ends of the divided cannula 10 are coupled to sensing and gas supply lines 32, 34, in a conventional manner, and to the gas supply system 36 so as to form both a pressure sensing flow path and a gas flow path between the patient's respiratory system and the gas supply system 36, via the divided cannula 10.

As shown in FIG. 6, the gas supply system 36 typically includes a breathing sensor system 30 connected to first one of the connection sections 26 or 28 of the divided cannula 10, e.g., the first connection section 26 in this Figure, via the pressure sensing line 32 in order to sense changes in pressure, generated during normal breathing of the patient, and control the supply of gas to the patient at the desired points in time when the supply of the gas to the patient is required or desired. The gas supply system 36 further includes a gas source 38 having a gas output connected to a gas controller 40 which, in turn, is coupled to and responsive to the breathing sensor system 30 for controlling the supply of gas from the gas source 38 to the other connection section 26 or 28, e.g., the second connection section 28 in this Figure, via the gas supply line 34.

According to this embodiment, the first divided body section 14 is connected via the first connection section 26 to the sensing line 32 and the second divided body section 16 is connected via the connection section 28 to the gas supply line 34. As a result of such connection, the first divided body section 14 functions as a cannula output flow path, that is, senses the fluctuations in pressure associated with the patient breathing and provides such sensed pressure information to the gas supply system 36, while the second divided body section 16 functions as a cannula input flow path, that is, supplies gas from the gas source 38 of the gas supply system 36 to the patient based upon the sensed pressure information.

The resulting flow paths through the divided cannula 10 and, in particular through the first and the second flow chambers 42 and 44 and through the first and the second nares 22 and 24, are generally as illustrated in FIGS. 4, 5 and 6. As illustrated therein, the patient's exhaled gases would, during the exhalation portion of the patient's breathing cycle, flow into the opening of the common nare passage 60 of each of the first and the second nares 22 and 24 and a portion of this exhaled gases would be diverted, by the flow diverter wall 66 of the first nare 22, so as to communicate with the first flow chamber 42 via the first nare passage 46 and also would be diverted, by the flow diverter wall 66 of the second nare 24, so as to communicate with the first flow chamber 42 via the second nare passage 48. The exhaled pressure information is then conveyed along and through the first divided body section 14, through the first connection section 26 along the sensing line 32 and eventually supplied as an input to the breathing sensor system 30 of the gas supply system 36. The gas supply system 36 would then determine, in a conventional manner based upon this supplied pressure information, the desired time to supply the gas to the patient via the gas source 38, the gas supply line 34 and the divided cannula 10.

During the inhalation portion of the patient's breathing cycle, when the gas source 38 of the gas supply system 36 is to supply a bolus of gas to the divided cannula 10, the gas flows along the gas supply line 34, through the second connection section 28, into the second divided body section 16 and through both the first and the second nare passages 59 and 52 into and through the common nare passage 60 of both the first and the second nares 22, 24 and finally into the patient's respiratory system via a respective one of the patient's nasal passages 18 and 20.

It will be understood and appreciated that the roles of the first and the second divided body section 14 and 16 may be reversed from that discussed above. That is, the first divided body section 14 may function as the supply path while the second divided body section 16 would function as the sensing path. Both of the first and the second nares 22 and 24 would each still simultaneously and concurrently function as both a sensing path as well as a supply path.

It will therefore be apparent that the divided cannula 10 of the present invention allows each nare 22 and 24 to operate as a pair of alternating gas flow paths, including an output flow path for collecting or sensing pressure changes due to breathing of the patient as well as an input flow path for supplying gas to the patient via the first and the second nares 22, 24 with the nares 22, 24 operating concurrently and in parallel with one another. As a result, the first and the second nares 22, 24 provide concurrently operating parallel gas flow paths through the divided cannula 10 to the patient and concurrently operating parallel gas flow paths through the divided cannula 10 from the patient, so that the blockage of one nare 22 or 24 will not halt or disrupt monitoring or control of the gas supply system with the divided cannula.

Lastly, a typical embodiment cannula body 12, exclusive of first and the second connection sections 26 and 28, has a width of approximately between about 0.9 and about 1.0 inches and the nares 22 and 24 are spaced apart from one another between about 0.65 and about 0.70 of an inch, for a typical adult sized divided cannula 10. The divided body sections 14 and 16 have exterior diameters of about 0.23 of an inch with the first and the second flow chambers 42 and 44 having interior diameters of about 0.13 of an inch. The first and the second flow chambers 42 and 44 are spaced apart from one another by the partitioning or dividing wall which has a thickness of about 0.04 inches. Each of the nare passages typically have a passage diameter of about 0.08 of an inch while the common passage typically has a diameter of between about 0.085 of an inch and about 0.130 of an inch.

Since certain changes may be made in the above described in the improved divided cannula, without departing from the spirit and scope of the invention herein involved, it is intended that all of the subject matter of the above description or shown in the accompanying drawings shall be interpreted merely as examples illustrating the inventive concept herein and shall not be construed as limiting the invention.

I claim:

1. A divided cannula comprising:
   a cannula body being divided by a partitioning wall into first and second internal flow chambers, each of the first and the second internal flow chambers having a first nare passage and a second nare passage;
   the cannula body supporting spaced apart first and second nares and each of the first and the second nares defining a common nare passage; and
   the first nare passages of the first and the send internal flow chambers communicate with the common nare passage of the first nare to facilitate a flow between an end of the common nare passage of the first nare remote from the cannula body and the first and the second internal flow chambers, the first nare passages of the first and the second internal flow chambers are separated from each other, within the first nare, by a first tapering flow diverter wall, and
   the second nare passages of the first and the second internal flow chambers communicate with the common nare passage of the second nare to facilitate a flow between an end of the common nare passage of the second nare remote from the cannula body and the first and the second internal flow chambers, the second nare passages of the first and the second internal flow chambers are separated from each other, within the second nare, by a second tapering flow diverter wall.

2. The divided cannula according to claim 1, wherein the cannula body has first and second connection sections, and the first connection section communicates with the first internal flow chamber and the second connection section communicates with the second internal flow chamber.

3. The divided cannula according to claim 2, wherein a pressure sensing line is connected with the first connection section and a gas supply line is connected with the second connection section and opposite ends of both the pressure sensing line and the gas supply line are connected with a gas supply system.

4. The divided cannula according to claim 3, wherein the gas supply system comprises a gas source connected with the gas supply line and a breathing sensor system connected with the pressure sensing line, and a gas controller is coupled to and responsive to the breathing sensor system for controlling a supply of the gas from the gas source to the divided cannula.

5. The divided cannula according to claim 1, wherein the first and the second nares are spaced apart from one another by a distance of between about 0.65 and about 0.70 inches.

6. A divided cannula comprising:

a cannula body being divided by a partitioning wall into first and second internal flow chambers;

the first internal flow chamber having first and second spaced apart nare passages;

the second internal flow chamber having first and second spaced apart nare passages;

the cannula body supporting spaced apart first and second nares and each of the first and the second nares defining a common nare passage; and the first nare passage of the first internal flow chamber and the first nare passage of the second internal flow chamber both communicate with the common nare passage of the first nare, the first nare passage of the first internal flow chamber and the first nare passage of the second internal flow chamber are separated from one another, within the first nare, by a first tapering flow diverter wall, the first nare passage of the first internal flow chamber and the first nare passage of the second internal flow chamber and the common nare passage of the first nare mate with one another so as to have a generally Y-shaped cross section; and the second nare passage of the first internal flow chamber and the second nare passage of the second internal flow chamber both communicate with the common nare passage of the second nare, and the second nare passage of the first internal flow chamber and the second nare passage of the second internal flow chamber are separated from one another, within the second nare, by a second tapering flow diverter wall, and the second nare passage of the first internal flow chamber and the second nare passage of the second internal flow chamber and the common nare passage of the second nare mate with one another so as to have a generally Y-shaped cross section.

7. The divided cannula according to claim 6, wherein the first and the second diverter walls are connected with the partitioning wall which partitions the cannula body into the first and the second internal flow chambers.

8. The divided cannula according to claim 6, wherein the partitioning wall, which partitions the cannula body into the first and the second internal flow chambers, extends generally axially along a longitudinal length of the divided cannula at least between the first and the second nares.

9. The divided cannula according to claim 6, wherein the cannula body comprises first and second divided body sections which are separated from one another by the partitioning wall with the first divided body section accommodating the first internal flow chamber and the second divided body section accommodating the second internal flow chamber, and the first divided body section at least partially overlaps the second divided body section between the first and the second nares.

10. A system for providing gas to a patient, comprising a divided cannula comprising a cannula body being divided by a partitioning wall into first and second internal flow chambers and the first internal flow chamber has a first connection section adjacent one end of the divided cannula and the second internal flow chamber has a second connection section adjacent another end of the divided cannula, the first internal flow chamber having first and second spaced apart nare passages, the second internal flow chamber having first and second spaced apart nare passages, the cannula body supporting spaced apart first and second nares and each of the first and the second nares defining a common nare passage, and the first nare passage of the first internal flow chamber and the first nare passage of the second internal flow chamber are separated from one another, within the first nare, by a first tapering diverter flow wall, and both communicate with the common nare passage of the first nare and the second nare passage of the first internal flow chamber and the second nare passage of the second internal flow chamber are separated from one another, within the second nare, by a second tapering diverter flow wall, and both communicate with the common nare passage of the second nare, and a pressure sensing line is connected with the first connection section and a gas supply line is connected with the second connection section and opposite ends of both the pressure sensing line and the gas supply line are connected with a gas supply system.

11. The system according to claim 10, wherein the gas supply system comprises a gas source connected with the gas supply line and a breathing sensor system connected with the pressure sensing line, and a gas controller is coupled to and responsive to the breathing sensor system for controlling a supply of the gas from the gas source to the divided cannula.

* * * * *